US007970098B2

(12) United States Patent
Haras

(10) Patent No.: US 7,970,098 B2
(45) Date of Patent: Jun. 28, 2011

(54) MEDICAL IMAGING METHOD AND APPARATUS ALLOWING LOCALIZED IMAGE QUALITY SPECIFICATION

(75) Inventor: Gabriel Haras, Muecke (DE)

(73) Assignee: Siemens Aktiengesellschaft, Munich (DE)

(*) Notice: Subject to any disclaimer, the term of this patent is extended or adjusted under 35 U.S.C. 154(b) by 162 days.

(21) Appl. No.: 12/406,196

(22) Filed: Mar. 18, 2009

(65) Prior Publication Data

US 2009/0238329 A1 Sep. 24, 2009

(30) Foreign Application Priority Data

Mar. 18, 2008 (DE) ........................ 10 2008 014 738

(51) Int. Cl.
*H05G 1/34* (2006.01)
*H05G 1/36* (2006.01)

(52) U.S. Cl. ........................................................ 378/16

(58) Field of Classification Search ..................... 378/16
See application file for complete search history.

(56) References Cited

U.S. PATENT DOCUMENTS 5,400,378 A * 3/1995 Toth ................................ 378/16
5,822,393 A * 10/1998 Popescu ........................ 378/108
5,867,555 A * 2/1999 Popescu et al. ................ 378/16
6,490,337 B1 * 12/2002 Nagaoka et al. ............... 378/20
6,754,301 B2 * 6/2004 Horiuchi ......................... 378/16
6,904,127 B2 * 6/2005 Toth et al. ....................... 378/16
6,987,828 B2 * 1/2006 Horiuchi ......................... 378/16
6,990,171 B2 * 1/2006 Toth et al. ....................... 378/16
7,103,139 B2 * 9/2006 Nagaoka et al. ................ 378/16
7,106,824 B2 * 9/2006 Kazama et al. ................. 378/16
7,142,630 B2 * 11/2006 Suzuki ........................... 378/16
7,203,270 B2 * 4/2007 Okumura et al. ............... 378/16
7,215,733 B2 * 5/2007 Nabatame ....................... 378/16
7,336,762 B2 * 2/2008 Seto et al. ....................... 378/16
7,519,155 B2 * 4/2009 Mollus et al. ................. 378/108
7,558,365 B2 * 7/2009 Wang ............................. 378/16
7,602,880 B2 * 10/2009 Hirokawa et al. ................ 378/8
7,636,416 B2 * 12/2009 Miyazaki et al. ............... 378/16
2002/0011844 A1 1/2002 Biglieri et al.

FOREIGN PATENT DOCUMENTS

DE 102 38 894 A1 3/2004

OTHER PUBLICATIONS

"Dosisreduktion durch Strommodulierte Dosisautomatik bei der MSCT: Vergleich von Messung und Rechnung," Lechel et al., Fortschr. Röntgenstr. (2007) p. 179.

* cited by examiner

*Primary Examiner* — Allen C. Ho
(74) *Attorney, Agent, or Firm* — Schiff Hardin LLP

(57) ABSTRACT

In a method and device for medical imaging, a number of input parameters with regard to an image exposure are imported into a controller of the imaging device, that associate a desired image quality with a defined image exposure region. A number of control parameters are determined corresponding to each input parameter. The controller supplies each control parameter to the image acquisition apparatus for acquiring the image exposure of the examination region with the desired local image quality.

22 Claims, 1 Drawing Sheet

18 20 4 14 18 20 4 14' 8 16 34 23 30 30 32 2 10 12 8 22 24 23 22' 24' 23 36 36 26 34 32 38 8 6

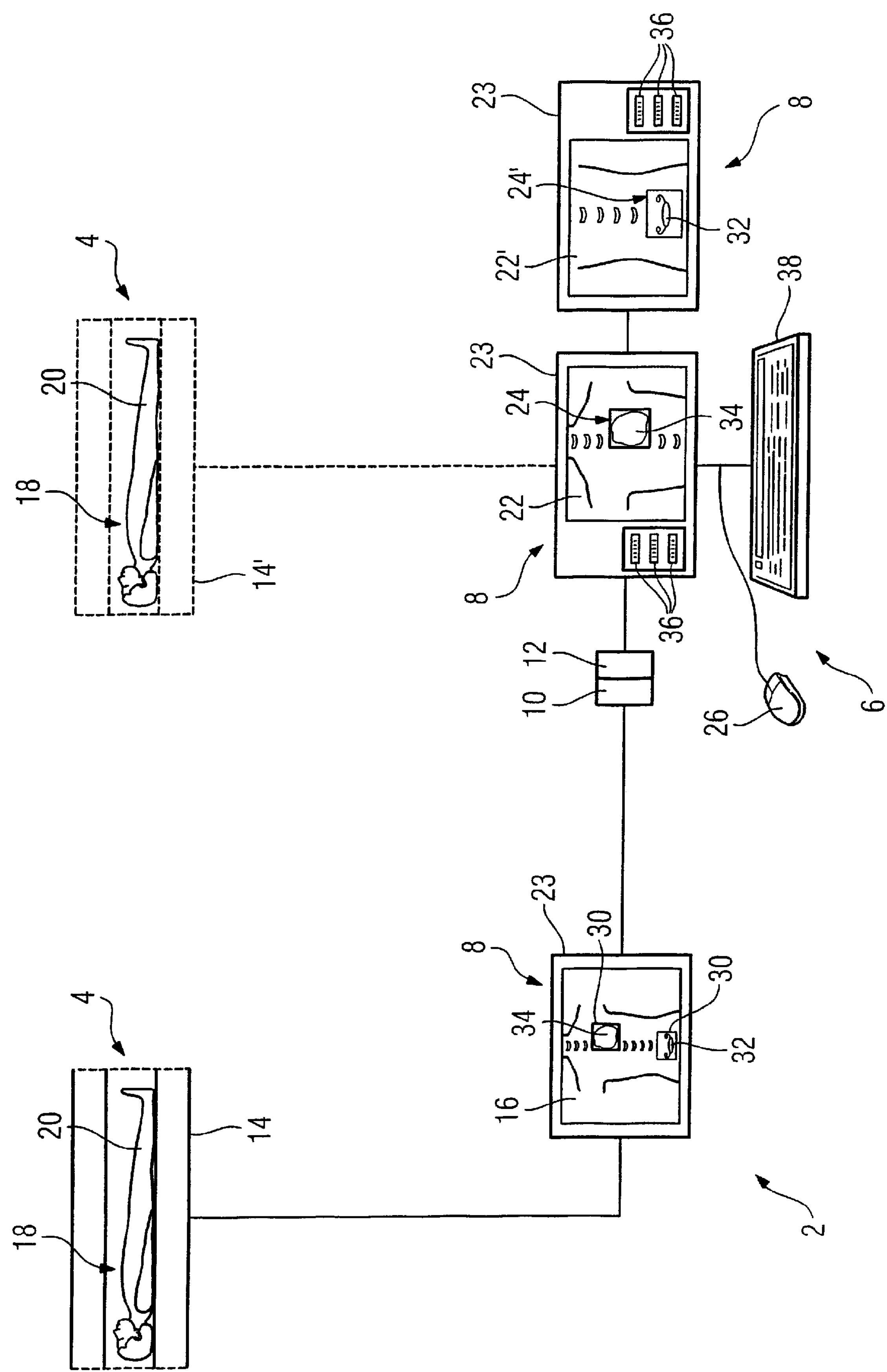
4
20
18
14'
23
36
8
24'
32
22'
38
24
34
22
12
10
26
6
30
16
14
2

MEDICAL IMAGING METHOD AND APPARATUS ALLOWING LOCALIZED IMAGE QUALITY SPECIFICATION

BACKGROUND OF THE INVENTION

1. Field of the Invention

The invention concerns a method for medical imaging as well as a corresponding medical imaging device.

2. Description of the Prior Art

Medical imaging is used for imaging, for implementing radiological examinations. In a radiological examination a subject (in particular a patient) is exposed with radiation. Electromagnetic beams or particle beams, for example x-rays or electrons, can be used for the exposure. As used herein, "an exposure" means radiograph of the patient.

Predominantly due to different local material properties of the tissue structures located in the beam path, the incident radiation is affected to different degrees in its passage through the body of the patient. In particular, different tissue structures have different radiation attenuation properties. This causes the beams passing through the body of the patient to be attenuated to different degrees. A detector signal corresponding to the intensity I of the attenuated beams can be generated by an appropriate detector. Such an attenuation is frequently defined as a logarithm of the ratio of the intensity of the attenuated beams to the intensity of the primary radiation ($\sim I/I_0$). The different tissue structures can be visualized as a projection using an attenuation distribution.

In tomography (for example x-ray computed tomography, also called CT for short) a plane of the subject (and in particular of the patient) is systematically radiographed from different directions, with the effect on the beams that are used (in particular their attenuation) is detected for each direction. Overall, a number of projections are thus acquired by means of which the attenuation distribution in the observed subject plane (and thus ultimately a spatial image exposure of said subject) is acquired.

The dose applied in such radiography of the patient with electromagnetic radiation is consistently the subject matter of intensive and critical discussions. The dose represents a measurement for the absorption of ionizing radiation (for example x-rays) by the exposed subject. In medicine, radiologically evaluated dose quantities are defined (for example in the form of an organ dose) to account for different radiation risks for various radiation types and for various tissue types.

The attempt is to keep the applied dose as low as possible proceeds according to the ALARA principle (ALARA=As Low As Reasonably Achievable).

Recently, current-modulated automatic dosing has increasingly been used, in particular in imaging by computed tomography. For example, such an automatic dosing can be learned from DE 102 38 894 A1 as well as in the article "Dosisreduktion durch strommodulierte Dosisautomatik bei der MSCT: Vergleich von Messung und Rechnung" ("Dose reduction via current-modulated automatic dosing in MSCT: Comparison of measurement and computation") by U. Lechel, C R Becker, G. Langenfeld-Jäger and G. Brix from Fortschritte auf dem Gebiet der Röntgenstrahlen und der bildgebenden Verfahren (Advances in the Field of X-rays and Imaging Methods), 2007 (179). An essentially constant image quality within an image exposure (in particular in the sense of a noise portion in the detector signal) is sought with such an automatic dosing. In order to achieve the constant image quality, the tube current of the computed tomography apparatus (and therefore the radiation power of its x-ray radiator) is frequently adapted to the locally different radiation attenuation relationships in the patient. The noise component in the image exposure is normally higher the fewer radiation quanta (in particular x-ray quanta) that are registered at the detector. It can also be stated more simply that the noise component is lower (and therefore the image quality is higher) given a high tube current than given a low tube current. Given a constant x-ray current, the noise component depends in particular on the existing radiation attenuation relationships in the patient. In a first approximation, the greater the radiation attenuation property, the higher the consequent noise component in the image exposure. The applied dose in turn linearly depends on, among other things, the x-ray current-time product. Essentially, by x-ray current modulation controlled by the image quality, as high a dose is applied as is necessary in order to achieve a noise component in the detector signal that is established corresponding to the predetermined image quality.

SUMMARY OF THE INVENTION

An object of the invention is to provide an alternative method for medical imaging with which a dose reduction can be achieved. An additional object is to provide a corresponding imaging device.

These objects are achieved in accordance with the invention by a method and apparatus wherein a number of input parameters with regard to an image exposure are imported into a processor that controls acquisition of an image that associate a desired image quality with a defined image exposure region. A number of control parameters are determined in the processor that corresponds to each input parameter. From the processor, each control parameter is supplied to an image acquisition apparatus and the image acquisition of an examination region is executed with the desired local image quality. The image exposure is executed by a computed tomography apparatus or a C-arm x-ray system.

The invention proceeds on the basis that the goal in conventional automatic dosing is essentially to achieve a constant image quality within an image exposure.

The invention is based on the insight that this is not always reasonable for medical considerations. Given a combined pelvis/torso image exposure in the framework of an examination of the liver of a patient, it is reasonable to achieve a high image quality in the region of the liver for which a relatively high dose must also be accepted in return. From a medical viewpoint, however, it is desirable to minimize a radiation exposure of the reproductive organs located in the pelvic region. Given the use of conventional automatic dosing, it is precisely this region that is particularly exposed since the radiation attenuation property in, for example, the region of the pelvic bone is particularly high, such that the tube current (and therefore the dose) is automatically increased by the automatic dosing in order to keep the image quality constant. The dose selected given a current-modulated automatic dosing thus primarily serves to control a constant image quality within the image exposure.

The invention proceeds in an entirely different way. Instead of aiming for a constant image quality within the entire image exposure, a desired higher or lower image quality can be locally associated with a defined image exposure region by means of the input parameter.

The invention thus enables the image quality to be varied in a targeted manner within an image exposure. This means in particular that targeted regions with a high image quality can lie next to regions with a lower image quality within an image exposure.

Medical considerations thus can also specifically be taken into account. For example, the image acquisition can be executed such that radiation-sensitive body parts are specifically protected in the scope of the imaging by these parts being imaged with a locally lower image quality. A locally low image quality in particular means that only a low dose is applied to these body regions in the scope of the imaging.

Overall this also opens the possibility to define radiation-sensitive body regions (for example the female breast, reproductive organs or marrow-containing bone regions of children) as risk regions that should in general be imaged with a low image quality, and thus in particular under application of a low dose.

By contrast, it is naturally also possible to define body regions that can and/or should be imaged with a very high image quality, for example the liver.

The desired image quality is predetermined by a number of input parameters. The corresponding input parameters can be manually predetermined by a physician, for example. Alternatively, it is naturally possible to automatically determine the input parameters which associate a corresponding image quality with the image acquisition of specific body regions. For example, the input parameters define and/or describe a noise proportion in the image exposure region, known as image noise. In modern image acquisition apparatuses (for example computed tomography apparatuses) the effect on the image noise due to the apparatus is negligibly small. The image noise is normally dominated by the quantum noise. Naturally, the desired image quality can alternatively or additionally also be predetermined by means of other input parameters. An input parameter that defines and/or describes a spatial resolution and/or a contrast resolution is an example. The capability of an imaging system to depict fine details with spatial separation is commonly described as the spatial resolution. The contrast resolution is typically understood as the ability to make details with low contrast recognizable. A low contrast recognition capability is predominantly determined by the noise level in the image exposure. In general, however, the image noise can be considered to be significant in determining the quality of the image exposure.

The image acquisition is, for example, a 2D image acquisition or a 3D image acquisition, which is executed by means of an imaging device, a computed tomography apparatus or a C-arm x-ray system. Naturally, multiple image acquisitions can be provided.

In the image acquisition the examination region is frequently imaged in very high detail. For example, the examination region may be the chest, the pelvis or the torso of a patient. The image acquisition region in particular specifies a region within the larger image exposure, for example the region of the liver in a torso image exposure or the region of the reproductive organs in a pelvis image exposure.

Existing patient data can be used to establish the image exposure region, for example. An "online" establishment during the radiography of the patient is also possible. For example, for this purpose an automatable algorithm for organ detection can be used. The image acquisition region of the liver, the reproductive organs or other organ structures can be automatically determined in this manner, for example.

A planning image exposure of the examination region is advantageously executed and displayed. Using the planning image exposure, an image region is selectively predetermined and the image exposure region is defined using the selected image region. The planning image exposure is in particular a 2D exposure which entirely or partially registers the examination region. Since normally no details need to be recognizable in the planning image exposure, the planning image exposure is frequently acquired with an image quality a great deal lower than the actual image exposure. The planning image exposure is appropriately executed in advance of the actual image exposure. It is particularly useful to execute the planning image acquisition and the image acquisition using the same image acquisition apparatus, so that no movement of the patient to another bed is necessary between the individual acquisitions. The planning image exposure is particularly suitable to establish the precise position of the defined image exposure region. For this purpose, the planning image exposure is shown, for example on a display device, for example a computer screen. The image region can be selected using the presented planning image exposure, for example by a physician selecting and marking the desired image region on the presentation device by means of a graphical user interface. Naturally, in this context it is likewise possible to automatically determine and mark the image exposure region, for example by means of a suitable algorithm for organ detection. The image exposure region with which the local image quality is associated is defined by the image region selected in the planning image exposure.

Multiple planning image exposures are advantageously executed that show various planes of the examination region using which a 2D image region can selectively be predetermined. For example, if multiple corresponding planning image exposures of the chest are available, in this embodiment the possibility exists to select a 2D image region comprising the heart in every shown plane so that a 3D image region results overall from this. The same image quality thus can be associated with each image exposure region corresponding to an image region plane. Naturally the association of different image qualities is hereby also possible. Overall the variability in the scope of a dose reduction is thereby additionally increased.

In another embodiment, the selected image region is overlaid on each planning image exposure. In the scope of this embodiment, the selected image region is, for example, marked by a semi-transparent color area. If multiple image regions are selected, the image regions that define image exposure regions with different image qualities can be marked with different colors, for example. A very low desired image quality can be marked with a strong red, for example, in order to call attention to particularly radiation-sensitive body regions. In this case a successively lighter red can be selected to indicate a higher image quality, for example. A physician is thus enabled to detect at a glance which image qualities are associated with which body regions to be imaged.

Each input parameter can be input directly. This in particular offers a physician the possibility to manually input the corresponding input parameters defining the desired image quality. The input advantageously ensues via a corresponding importation device (for example a keyboard of a computer) or by means of a mouse pointer via a graphical user interface.

As already mentioned, the image noise is frequently considered to be decisive in determining the quality of the image. In general, the fewer the radiation quanta (in particular x-ray quanta) that are registered at the detector, the more the image noise rises. The noise proportion in the image exposure in particular also rises given a low current-time product; the noise level changes with the square root of this parameter. For a computed tomography apparatus, the designation "tube current" is more often used instead of the designation "current".

Due to the given dependency of the image quality on the current-time product, in a preferred embodiment a current-time product value is imported as a quality parameter. For example, by means of the current-time product value it is also possible to quickly estimate the applied dose. The dose namely essentially linearly depends on the current-time product. The current-time product is normally specified in the unit [mAs].

In an alternative embodiment, a normalized input parameter is imported. In particular a normalized input parameter is predetermined by such a normalized input parameter, which normalized input parameter is evaluated (for example using measurements on a measurement phantom) and is frequently referred to as an "average patient". Using the normalized input parameter, it is not necessary for a physician to explicitly take into account the size and weight of a patient to be examined, for example, into account in the selection of the input parameter. Rather, in this embodiment it is possible for the physician simply to select the normalized input parameter, for example in the form of a normalized current-time product. A modification of the current time product that is adapted to the corresponding patient normally ensues automatically. Overall, reference to a defined reference system is enabled through the use of the normalized input parameter, which allows different measurements to be done in a manner facilitating comparison of the images.

A percentile value of the normalized input parameter is advantageously imported as an input parameter. The percentile value indicates the desired image quality, in particular relative to the normalized image quality. This simplifies the operability and clarity for the user.

In a further embodiment, the value of the or each input parameter is stored. In particular the selected current-time product value is stored. For example, in this embodiment an automated generation of an acquisition protocol can ensue as to the image quality and the applied dose for individual, displayed body regions. This can be used both for documentation purposes and for independent monitoring.

An apparatus current of the image acquisition apparatus is advantageously modulated by each control parameter, corresponding to the desired image quality. As described above, the image quality can be directly correlated with the current-time product. For this reason it is suggested to adjust the image quality by a modulation of the apparatus current of the image acquisition apparatus, for example of the tube current of the computed tomography apparatus.

A control parameter corresponding to an increased apparatus current is advantageously determined for a higher image quality. The expediency of this embodiment is due to the dependency of the noise component in the image exposure on the current-time product. The noise level is lower the greater the current-time product. This can be effectively achieved by increasing the current (thus the apparatus current).

A maximum value for the input parameter is advantageously imported. This maximum value can be value that, for example, artificially limits the system power limit of the image acquisition apparatus. For example, if the maximum achievable tube current-time product is 500 mAs, the usable system power limit of the image acquisition apparatus can be artificially limited by selecting (setting) a maximum value for the input parameters (in the form of a normalized current-time product, for example). This can be particularly useful for medical considerations in order to limit a radiation exposure of a child, for example. In this embodiment, medical considerations can be taken into account that are specific to the patient.

A computed tomography image acquisition is preferably implemented as the image acquisition. A computed tomography apparatus thus is used as the image acquisition apparatus. Computed tomography apparatuses are widely used in medical imaging, and thus represent a mature technology.

The medical imaging accordingly has an image acquisition apparatus, an importation device and a control device. The importation device is configured to import a number of input parameters that associate a desired image quality with a defined image exposure region. The control device is configured to determine a number of control parameters corresponding to each input parameter and to control the image acquisition apparatus by means of each control parameter to execute a image acquisition of an examination region. The image acquisition apparatus is configured to implement an image acquisition of the examination region with the desired local image quality. The image acquisition apparatus is a computed tomography apparatus or a C-arm x-ray system.

The advantages described above apply to the imaging device, as well as the method.

The importation device may be a device to import external data, for example a CD-ROM drive. Alternatively or additionally, the importation device can be (for example) a keyboard or a graphical user interface of a computer via which a physician can manually input the input parameter, for example.

The control device can be a control module or a computer, for example, employing software embodying programming instructions to implement the method described above.

A presentation device is advantageously provided that is suitable for presentation of the planning image exposure and, if necessary, also for presentation of the actual image exposure. The presentation device is, for example, a monitor of the computer.

A memory element is advantageously provided which is suitable for storage of the selected current-time product value. The memory element can be realized on a hard drive of a computer, for example.

BRIEF DESCRIPTION OF THE DRAWING

The single FIGURE schematically illustrates an imaging system constructed and operating in accordance with the present invention.

DESCRIPTION OF THE PREFERRED EMBODIMENTS

The method workflow of an embodiment of the method according to the invention will be explained using the illustration of the medical imaging device 2 in the FIGURE.

The imaging device 2 has an image acquisition apparatus 4, an importation device 6, a control device 10, and a memory element 12.

The image acquisition apparatus 4 is a computed tomography apparatus 14, called a CT apparatus 14 in the following. The CT apparatus 14 has an x-ray source and a detector (not shown), in particular in the form of a detector ring. The x-ray source and the detector are arranged opposite one another. The CT apparatus 14 is configured to implement an image acquisition 16 of an examination region 18 of a patient 20 as well as to obtain a number of planning image exposures (images) 22, 22'. Both the image acquisition 16 and the planning images 22, 22' are visualized here on the presentation device 8 executed as a computer monitor 23.

The image exposure 16 is a three-dimensional CT scan of the examination region 18 of the patient 20. To generate the 3D image exposure 16, the x-ray source and the detector of the CT apparatus 14 rotate around the patient 20. A number of slices of the patient 20 are thereby systematically radiographed from different directions by the x-rays. The x-rays passing through the patient and attenuated by the passage strike the detector, which thereupon generates detector signals that correspond to the intensity of the attenuated beams. Due to locally different material properties of the tissue structures in the beam path (for example organs, bones etc.), the incident radiation is attenuated to different degrees upon passage through the body of the patient 20, such that a 3D image exposure 16 of the patient 20 can be determined and presented using the detector signals.

The planning image exposures 22, 22' and the image exposure 16 are respectively acquired with the same CT apparatus 14, so that no movement of the patient 20 to a different bed is necessary between the execution of the individual acquisitions. The dashed representation of the CT apparatus 14' indicates that the planning image exposures 22, 22' were acquired in the past (i.e., prior to the exposure 16).

The planning image exposures 22, 22' are 2D image exposures. The corresponding 2D image exposures are executed with a stationary x-ray source, similar to a conventional x-ray exposure. The planning image exposures 22, 22' respectively show different sections of the examination region 18 of the patient 20 in the manner of an overview. The planning image exposure 22 here shows a torso region of the patient 20 while the other image exposure 22' shows a pelvic region of the patient 20.

Using the planning image exposures 22, 22', image regions 24, 24' are respectively manually selected by a physician by means of the importation device 6. For this purpose, the importation device 6 has a graphical user interface so that the relevant image region 24, 24' can be placed on the computer monitor 23 by means of a computer mouse 26.

The selected image region 24' in the planning image exposure 22' (which shows the pelvic region of the patient 20) defines the ovaries 32 of the female patient 20; the other image region 24 in the planning image exposure 22 (which shows the torso region of the patient) defines the heart 34 of the patient 20. The selected image regions 24, 24' are respectively overlaid in the corresponding planning image exposure 22, 22' as a semi-transparent color overlay. The selected image regions 24, 24' are thus quickly visually detectable and reviewable for a physician.

Using the selected image regions 24, 24', the control device 10 defines an image exposure region 30 in the image exposure 16. In the scope of an execution of the image exposure 16, the control device 10 then controls the CT apparatus 14 such that it executes the image exposure 16 with a desired local image quality in the image exposure region 30. For this purpose, the control device 10 modulates an apparatus current (here in particular a tube current of the CT apparatus 14) corresponding to the desired image quality, such that the tube current of the CT apparatus 14 is increased for a higher image quality.

In this context "local image quality" means that the image exposure 16 is not acquired with a constant image quality. An image quality that is significantly lower than that of the remaining image exposure 16 is associated with the image region 30 that contains the ovaries 32 of the female patient 20. A high image quality is associated with the image exposure region 30 that contains the heart 34 of the patient.

The corresponding desired image qualities of the image exposure region 30 are defined by a number of input parameters, which are imported in advance of the execution of the image exposure 16.

A corresponding importation of the input parameters ensues via the graphical user interface of the importation device 6. For this purpose, the graphical user interface has a number of input fields 36 in which, for example, a physician directly inputs the input parameters with the assistance of a computer keyboard 38 of the importation device 6. One of the input fields 36 is also provided for an input of a maximum value of the input parameter.

The input parameters can include a normalized input parameter, in particular a normalized current-time product. The normalized current-time product is referenced to an "average patient". A corresponding adaptation with regard to the size and the weight of the concrete patient to be examined ensues automatically in the control device 10. Alternatively or additionally, the input parameters can likewise be input as a percentile value of the normalized input parameter. The percentile value indicates the desired image quality, in particular relative to the normalized image quality.

The maximum value is likewise input as a normalized current-time product. Here a value of 300 mAs is input as a maximum value.

Corresponding to the selection of the input parameters defining the image qualities, a color is associated with the semi-transparent overlays that are overlaid in the planning image exposures 22, 22' on the selected image regions 24, 24': a dark red color is associated with the image region 24' containing the ovaries 32, corresponding to the very low desired image quality, and a blue color is associated with the image region 24 containing the heart 34 due to the high desired image quality. Which image quality was associated with which image exposure region 30 is therefore qualitatively apparent to a physician at first glance.

The selection of the local image qualities embodies (represents) a selection of the radiation dose applied to the patient 20 during the CT scan. This is due to the given radiation between the image quality and the applied dose: the image quality is strongly dependent on the noise component in the image exposure 16. In general, the noise component in the image exposure 16 increases with a decreasing current-time product. In the CT apparatus 14, the term "current" designates the CT tube current. Since the dose applied to the patient 20 during the CT scan essentially linearly depends on the current-time product, a simple correlation exists between the image quality and the applied dose: the higher the image quality, the higher that the applied dose also normally is, and vice versa.

The dose also constitutes a measurement of the absorption of x-rays by the radiographed tissue of the patient 20. In medicine, dose quantities (for example in the form of an organ dose) that take different radiation risks for various tissue types into account are frequently used.

The selection of a low image quality for the image exposure region 30 that contains the ovaries 32 of the patient 20 allows a low dose to be applied to the ovaries 32. This is reasonable from a medical viewpoint since the ovaries 32 are particularly radiation-sensitive and are especially to be protected from the point of view of genetic damage.

In the area of the heart 34, it can be reasonable in the scope of an imaging to achieve a high image quality. However, in order to protect the radiation-sensitive region of the female breast, for example, the corresponding "high quality" image region 30 is narrowly defined so that no unnecessary radiation exposure of surrounding tissue structures occurs.

In addition to the desired image quality, the physician can input a number of CT apparatus variables in the input fields 36, which CT apparatus variables are relevant within the scope of the CT scan. Typical scan parameters (for example, the scan time, the CT tube voltage, the number of slices and the slice thickness) are examples of such apparatus variables.

For documentation purposes, storage of all relevant variables can take place in the memory element 12, namely storage of the apparatus variables, the input parameters and the maximum value.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for operating medical imaging apparatus selected from the group consisting of computed tomography apparatuses and C-arm x-ray apparatuses, that obtains a medical image exposure of a patient, said medical image exposure encompassing a plurality of regions in the patient, comprising the steps of:

defining a plurality of input parameters, dependent on a normalized input parameter, that respectively associate a desired image quality with said regions;

defining a plurality of control parameters respectively corresponding to the input parameters, that respectively control irradiation of the respective regions by said medical imaging apparatus; and operating said medical imaging apparatus according to said control parameters to obtain an image exposure comprising said regions with each region receiving a localized radiation dose that causes that region to have an image quality in the overall image exposure as defined by an input parameter for that region among said plurality of input parameters.

2. A method as claimed in claim 1 comprising:

with said medical imaging apparatus, obtaining a planning image exposure of the patient, and displaying said planning image exposure;

selecting at least one of said regions by interacting with the displayed planning image exposure; and automatically defining said radiation dose in said overall image exposure dependent on said at least one of said regions selected in said planning image exposure.

3. A method as claimed in claim 2 comprising obtaining a plurality of planning image exposures in respectively different planes of the patient, and generating a 3D planning image exposure therefrom.

4. A method as claimed in claim 2 comprising symbolically overlaying the selected region in said planning image exposure.

5. A method as claimed in claim 1 comprising manually entering each input parameter into a controller of said medical imaging apparatus.

6. A method as claimed in claim 1 comprising entering a current-time product value as each input parameter for each region.

7. A method as claimed in claim 1 comprising determining said input parameters as respective percentile values of said normalized input parameter.

8. A method as claimed in claim 1 comprising storing respective values of each input parameter.

9. A method as claimed in claim 1 wherein said medical imaging apparatus operates with an apparatus current, and modulating said apparatus current by means of the respective control parameters to achieve the desired image quality in the respective regions.

10. A method as claimed in claim 9 comprising employing an increased apparatus current to achieve a higher image quality.

11. A method as claimed in claim 1 comprising limiting each input parameter to a maximum value.

12. A medical imaging system comprising:

a medical image acquisition apparatus selected from the group consisting of computed tomography apparatuses and C-arm x-ray apparatuses, that obtains a medical image exposure of a patient, said medical image exposure encompassing a plurality of regions in the patient;

a computer supplied with a plurality of input parameters, that are defined dependent on a normalized input parameter, that respectively associate a desired image quality with said regions;

said computer being configured to define a plurality of control parameters respectively corresponding to the input parameters, that respectively control irradiation of the respective regions by said medical image acquisition apparatus; and said computer being configured to operate said medical image acquisition according to said control parameters to obtain an image exposure comprising said regions with each region receiving a localized radiation dose that causes that region to have an image quality in the overall image exposure as defined by an input parameter for that region among said plurality of input parameters.

13. A medical imaging system as claimed in claim 12 wherein said computer is further configured to:

operate said medical image acquisition apparatus to obtain a planning image exposure of the patient, and display said planning image exposure;

select at least one of said regions by interacting with the displayed planning image exposure; and automatically define said radiation dose in said overall image exposure dependent on said at least one of said regions selected in said planning image exposure.

14. A medical imaging system as claimed in claim 13 wherein said computer is further configured to operate said medical imaging apparatus to obtain a plurality of planning image exposures in respectively different planes of the patient, and to generate a 3D planning image exposure therefrom.

15. A medical imaging system as claimed in claim 13 wherein said computer is configured to symbolically overlay the selected region in said planning image exposure.

16. A medical imaging system as claimed in claim 12 comprising an input unit in communication with said computer that allows manual entry of each input parameter into said computer.

17. A medical imaging system as claimed in claim 12 wherein said computer is provided with a current-time product value as each input parameter for each region.

18. A medical imaging system as claimed in claim 12 wherein said computer is configured to determine said input parameters as respective percentile values of said normalized input parameter.

19. A medical imaging system as claimed in claim 12 wherein said computer is configured to store respective values of each input parameter.

20. A medical imaging system as claimed in claim 12 wherein said medical image acquisition apparatus operates with an apparatus current, and wherein said computer is configured to modulate said apparatus current by means of the respective control parameters to achieve the desired image quality in the respective regions.

21. A medical imaging system as claimed in claim 20 wherein said computer is configured to employ an increased apparatus current to achieve a higher image quality.

22. A medical imaging system as claimed in claim 12 wherein said computer is configured to limit each input parameter to a maximum value.

* * * * *